(12) United States Patent
Gross

(10) Patent No.: US 7,818,062 B2
(45) Date of Patent: Oct. 19, 2010

(54) PERISTALTIC PUMP FOR TREATMENT OF ERECTILE DYSFUNCTION

(75) Inventor: Yossi Gross, Moshav Mazor (IL)

(73) Assignee: Ed Tech Medical Ltd., Herzliya (IL)

( * ) Notice: Subject to any disclaimer, the term of this patent is extended or adjusted under 35 U.S.C. 154(b) by 143 days.

(21) Appl. No.: 12/023,900

(22) Filed: Jan. 31, 2008

(65) Prior Publication Data

US 2009/0198097 A1 Aug. 6, 2009

(51) Int. Cl.
*A61N 1/18* (2006.01)

(52) U.S. Cl. .......................... 607/39; 607/143; 600/40; 600/38

(58) Field of Classification Search .................. 607/39, 607/143; 128/788; 600/38–40
See application file for complete search history.

(56) References Cited

U.S. PATENT DOCUMENTS

| | | | |
|---|---|---|---|
| 3,827,426 A | 8/1974 | Page et al. | |
| 3,885,251 A | 5/1975 | Pedroso | |
| 4,829,990 A | 5/1989 | Thuroff et al. | |
| 4,982,731 A | 1/1991 | Lue et al. | |
| 5,048,511 A | 9/1991 | Rosenbluth et al. | |
| 5,192,271 A * | 3/1993 | Kalb et al. | 604/116 |
| 5,324,323 A | 6/1994 | Bui | |
| 5,328,460 A | 7/1994 | Lord et al. | |
| 5,372,573 A | 12/1994 | Habib | |
| 5,645,839 A | 7/1997 | Chobanian et al. | |
| 5,800,502 A | 9/1998 | Boutos | |
| 5,900,433 A | 5/1999 | Igo et al. | |
| 5,904,712 A | 5/1999 | Axelgaard | |
| 6,023,640 A | 2/2000 | Ross | |
| 6,038,485 A | 3/2000 | Axelgaard | |
| 6,058,331 A | 5/2000 | King | |
| 6,086,527 A | 7/2000 | Talpade | |
| 6,200,259 B1 | 3/2001 | March | |
| 6,347,247 B1 | 2/2002 | Dev et al. | |
| 6,463,323 B1 | 10/2002 | Conrad-Vlasak et al. | |
| 6,679,832 B1 | 1/2004 | Sultan | |

(Continued)

FOREIGN PATENT DOCUMENTS

EP   0109935   5/1984

(Continued)

OTHER PUBLICATIONS

Ball, G. et al., "A Miniature Peristaltic Pump with Electronic Rate Control: Technical Adaption to a Clinical need", Biomed Eng. 9(12); 563-5 (1974).

(Continued)

*Primary Examiner*—Carl H Layno
*Assistant Examiner*—Paula J Stice
(74) *Attorney, Agent, or Firm*—Fish & Richardson P.C.

(57) ABSTRACT

In some embodiments of the present invention, apparatus is provided for treating erectile dysfunction of a subject. The apparatus includes one or more electrodes configured to be coupled to a vicinity of a blood vessel that carries blood into or out of a penis of the subject, and a control unit configured to facilitate erection of the penis by peristaltically pumping blood in the blood vessel by stimulating nitric oxide (NO) production in the vicinity, by driving the electrodes to drive a current into the vicinity. Additional embodiments are also described.

20 Claims, 3 Drawing Sheets

U.S. PATENT DOCUMENTS

| | | |
|---|---|---|
| 6,706,682 B2 | 3/2004 | Shabsigh |
| 6,810,286 B2 | 10/2004 | Donovan et al. |
| 6,824,561 B2 | 11/2004 | Soykan et al. |
| 6,845,267 B2 | 1/2005 | Harrison et al. |
| 6,865,416 B2 | 3/2005 | Dev et al. |
| 6,871,092 B2 | 3/2005 | Piccone |
| 6,885,895 B1 | 4/2005 | Whitehurst et al. |
| 6,939,345 B2 | 9/2005 | KenKnight et al. |
| 7,206,637 B2 | 4/2007 | Salo |
| 7,229,403 B2 | 6/2007 | Schock et al. |
| 2001/0044434 A1* | 11/2001 | Lee et al. ............... 514/217.03 |
| 2002/0055761 A1* | 5/2002 | Mann et al. ................... 607/41 |
| 2002/0103454 A1 | 8/2002 | Sackner et al. |
| 2003/0036773 A1 | 2/2003 | Whitehurst et al. |
| 2003/0191512 A1* | 10/2003 | Laufer et al. ................ 607/101 |
| 2003/0204206 A1 | 10/2003 | Padua et al. |
| 2004/0039417 A1 | 2/2004 | Soykan et al. |
| 2004/0054384 A1 | 3/2004 | Nachum |
| 2004/0106954 A1 | 6/2004 | Whitehurst et al. |
| 2004/0193228 A1* | 9/2004 | Gerber ........................ 607/39 |
| 2005/0209652 A1* | 9/2005 | Whitehurst et al. ........... 607/39 |
| 2005/0233962 A1 | 10/2005 | Lue et al. |
| 2005/0240229 A1 | 10/2005 | Whitehurst et al. |
| 2006/0100668 A1 | 5/2006 | Ben-David et al. |
| 2006/0149345 A1* | 7/2006 | Boggs et al. ................ 607/118 |
| 2006/0173507 A1* | 8/2006 | Mrva et al. .................... 607/39 |
| 2006/0206149 A1* | 9/2006 | Yun ............................... 607/3 |
| 2006/0276844 A1 | 12/2006 | Alon et al. |
| 2007/0179559 A1* | 8/2007 | Giftakis et al. ................ 607/46 |
| 2010/0016657 A1* | 1/2010 | Robertson et al. ............. 600/41 |

FOREIGN PATENT DOCUMENTS

| | | |
|---|---|---|
| WO | 8401905 | 5/1984 |
| WO | 2004/014456 | 2/2004 |
| WO | WO-2005074384 | 8/2005 |
| WO | 2006/064503 | 6/2006 |
| WO | 2006/094273 | 9/2006 |
| WO | 2006/123346 | 11/2006 |
| WO | 2007/013065 | 2/2007 |
| WO | 2007/064895 | 6/2007 |
| WO | 2007/106533 | 9/2007 |
| WO | 2007/113833 | 10/2007 |

OTHER PUBLICATIONS

Hayashida, et al., "Comparison of neurogenic contraction and relaxation in canine corpus cavernosum and penil artery and vein", Jpn. J. Pharmacol. 72:231-240 (1996), p. 232, col. 2, para 1; p. 238, col. 2, para 2.

* cited by examiner

PERISTALTIC PUMP FOR TREATMENT OF ERECTILE DYSFUNCTION

FIELD OF THE INVENTION

The present invention generally relates to medical apparatus and methods. Specifically, the present invention relates to medical apparatus and methods for treating erectile dysfunction.

BACKGROUND OF THE INVENTION

An erection is caused by an influx of blood into sponge-like regions of tissue in the penis. The increased volume of blood in the penis causes it to become rigid and to increase in length and diameter. Many males suffer from erectile dysfunction. This condition is characterized by an inability to develop or maintain an erection that is of sufficient strength or duration to allow normal sexual intercourse.

U.S. Pat. No. 6,023,640 to Ross, which is incorporated herein by reference, describes the use of electromagnetic therapy to align the nutrients of the blood in a pearl cell formation in the direction of arterial flow. This is described as contributing, because of lessened flow resistance, to an increased volume of blood adequate for penis-engorgement.

U.S. Pat. No. 6,885,895 to Whitehurst, which is incorporated herein by reference, describes systems and methods for introducing one or more stimulating drugs and/or applying electrical stimulation to tissue affecting the penis to treat erectile dysfunction (for instance, following prostate surgery). The systems and methods are described as using at least one implantable system control unit (SCU) producing electrical pulses delivered via electrodes and/or producing drug infusion pulses, wherein the stimulating drug(s) are delivered via one or more pumps and infusion outlets.

PCT Publication WO 07/013065 to Gross, which is incorporated herein by reference, describes apparatus that includes a bifurcation stent comprising one or more electrodes, the stent configured to be placed in a primary passage and a secondary passage of a blood vessel, and a control unit, configured to drive the electrodes to apply a signal to a wall of the blood vessel, and to configure the signal to increase nitric oxide (NO) secretion by the wall. In an embodiment, the applied signal is described as being used to treat erectile dysfunction by functioning as a pump to enhance blood flow (e.g., for a diabetic patient), and/or by generating NO as a signaling molecule which enhances erection.

U.S. Pat. No. 5,372,573 to Habib, which is incorporated herein by reference, describes a method and apparatus for improving the flow of blood through a region of increased impedance. The method comprises assisting blood flow in said region by means of a pump placed in or around a blood vessel supplying blood to said region, and acting to pump blood in the required direction. The pump comprises, in one embodiment, a housing annularly surrounding a compressible conduit, said housing containing a plurality of flexible inflatable containers mounted for contact with said conduit (e.g., a blood vessel) and means for effecting sequential inflation and deflation of said containers so as to create a peristaltic pumping effect.

The following patents and patent applications, which are incorporated herein by reference, may be of interest:
U.S. Pat. No. 5,324,323 to Bui
U.S. Pat. No. 5,645,839 to Chobanian et al.
U.S. Pat. No. 5,800,502 to Boutos
U.S. Pat. No. 5,900,433 to Igo et al.
U.S. Pat. No. 5,904,712 to Axelgaard
U.S. Pat. No. 6,038,485 to Axelgaard
U.S. Pat. No. 6,058,331 to King
U.S. Pat. No. 6,086,527 to Talpade
U.S. Pat. No. 6,200,259 to March
U.S. Pat. No. 6,347,247 to Dev et al.
U.S. Pat. No. 6,463,323 to Conrad-Vlasak et al.
U.S. Pat. No. 6,810,286 to Donovan et al.
U.S. Pat. No. 6,824,561 to Soykan
U.S. Pat. No. 6,845,267 to Harrison et al.
U.S. Pat. No. 6,865,416 to Dev et al.
U.S. Pat. No. 6,871,092 to Piccone
U.S. Pat. No. 6,939,345 to KenKnight et al.
U.S. Pat. No. 7,206,637 to Salo
U.S. Pat. No. 7,229,403 to Schock et al.
US 2002/0103454 to Sackner et al.
US 2003/0036773 to Whitehurst et al.
US 2003/0204206 to Padua et al.
US 2004/0039417 to Soykan et al.
US 2004/0106954 to Whitehurst et al.
US 2006/0276844 to Alon
PCT Publication WO 04/014456 to Allen et al.
PCT Publication WO 06/094273 to White et al.
PCT Publication WO 07/064895 to Meyerhoff et al.
PCT Publication WO 07/106533 to Stern et al.
PCT Publication WO 07/113833 to Cahan et al.
PCT Publication WO 2006/064503 to Belsky et al.
PCT Publication WO 2006/123346 to Alon et al.
European Patent Application Publication EP 0 109 935 A1 to Charmillot et al.

SUMMARY OF THE INVENTION

In some embodiments of the invention, one or more electrodes are coupled to a vicinity of an artery that supplies a penis of the subject. A control unit drives the electrodes to drive a current into the vicinity of the artery. The current is configured to cause peristaltic pumping of blood toward the penis by stimulating nitric oxide (NO) production in the vicinity of the artery, such that nitric oxide production causes the artery to dilate in peristaltic waves.

Typically, the current has a frequency that is between 5 Hz and 20 Hz, e.g., between 10 Hz and 15 Hz. Further typically, the current has an amplitude that is between 0.1 mA and 5 mA, e.g., between 2 mA and 3 mA.

In some embodiments, the electrodes are configured to be implanted inside the artery. Alternatively or additionally, the electrodes are configured to be implanted outside of the artery. Further alternatively or additionally, the electrodes are configured to be placed on skin of the subject, for example, around the outside of the subject's penis.

In some embodiments, the control unit is configured to receive an input from the subject and to initiate the pumping of blood toward the penis in response to receiving the input. Alternatively or additionally, the control unit is configured to initiate the pumping of blood toward the penis in response to receiving an input from a sensor.

There is therefore provided in accordance with an embodiment of the invention, apparatus for treating erectile dysfunction of a subject, including:
one or more electrodes configured to be coupled to a vicinity of a blood vessel that carries blood into or out of a penis of the subject; and
a control unit configured to facilitate erection of the penis by peristaltically pumping blood in the blood vessel by stimulating nitric oxide (NO) production in the vicinity, by driving the electrodes to drive a current into the vicinity.

In an embodiment, the blood vessel includes a vein, and the control unit is configured to facilitate the erection by inhibiting blood from leaving the penis by peristaltically pumping the blood.

In an embodiment, the blood vessel includes an artery, and the control unit is configured to facilitate the erection by peristaltically pumping the blood distally in the artery.

In an embodiment, the control unit is additionally configured to apply a contraction-inducing current at a site proximal to a site in which the control unit is stimulating nitric oxide production.

In an embodiment, the apparatus further includes one or more venous electrodes configured to be coupled to a vicinity of a vein that is supplied by blood from the penis of the subject, and the control unit is configured to reduce outflow of blood from the penis by peristaltically pumping the vein by stimulating nitric oxide (NO) production in the vicinity of the vein, by driving the venous electrodes to drive a current into the vicinity of the vein.

In an embodiment, the control unit is configured to reduce outflow of blood from the penis by peristaltically pumping a vein that is supplied by blood from the subject's penis, by stimulating nitric oxide (NO) production in a vicinity of the vein, by driving the electrodes to drive a current into the vicinity of the vein.

In an embodiment, the control unit is configured to operate independently of a cardiac cycle of the subject.

In an embodiment, the control unit is configured to receive an input from the subject and to initiate the pumping of blood toward the penis in response to receiving the input.

In an embodiment, the artery includes a dorsal artery of the penis of the subject, and the one or more electrodes are configured to be coupled to a vicinity of the dorsal artery of the penis of the subject.

In an embodiment, the artery includes an internal iliac artery of the subject, and the one or more electrodes are configured to be coupled to a vicinity of the internal iliac artery of the subject.

In an embodiment, the artery includes an internal pudendal artery of the subject, and the one or more electrodes are configured to be coupled to a vicinity of the internal pudendal artery of the subject.

In an embodiment, the control unit is configured to drive the electrodes to drive a current having a frequency of 5-15 Hz into the vicinity.

In an embodiment, the control unit is configured to drive the electrodes to drive a current having an amplitude of 1-5 mA into the vicinity.

In an embodiment, the one or more electrodes include at least three electrodes, configured to be coupled to respective longitudinal positions along the artery such that a spacing between one of the three electrodes and another one of the three electrodes is between 1 cm and 4 cm.

In an embodiment, the one or more electrodes include at least three electrodes, and the apparatus further includes a housing to which the at least three electrodes are coupled, which is configured to maintain a longitudinal distance between one of the three electrodes and another one of the three electrodes that is between 1 cm and 4 cm.

In an embodiment, the control unit is configured to set a duration of one cycle of peristaltic pumping to be between 0.25 second and 2 seconds.

In an embodiment, the one or more electrodes are configured to be implanted inside the artery.

In an embodiment, the control unit is configured to operate in coordination with a cardiac cycle of the subject.

In an embodiment, the control unit is configured to peristaltically pump the blood by stimulating the nitric oxide production during systole, and to apply a contraction-inducing current into the vicinity during diastole.

In an embodiment, the one or more electrodes are configured to be implanted outside of the artery.

In an embodiment, the one or more electrodes are configured to be implanted in a corpus cavernosum of the penis of the subject.

In an embodiment, the one or more electrodes are configured to be implanted in a corpus spongiosum of the penis of the subject.

In an embodiment, the one or more electrodes are configured to be placed on skin of the subject and to drive the current through the skin.

In an embodiment, the one or more electrodes are configured to be placed around the outside of the penis of the subject.

In an embodiment, the apparatus further includes a patch, the one or more electrodes are disposed on the patch, and the patch is configured to be secured to the skin.

In an embodiment, the apparatus further includes a sensor, and the control unit is configured to receive an input from the sensor and to initiate the pumping of blood toward the penis in response to receiving the input from the sensor.

In an embodiment, the sensor includes at least one sensor selected from the group consisting of: a blood flow detector, a chemical detector, and a sensing electrode.

There is additionally provided, in accordance with an embodiment of the invention, a method for treating erectile dysfunction of a subject, including:

coupling one or more electrodes to a vicinity of a blood vessel that carries blood into or out of a penis of the subject; and facilitating erection of the penis by peristaltically pumping blood in the blood vessel by stimulating nitric oxide (NO) production in the vicinity by driving the electrodes to drive a current into the vicinity.

The present invention will be more fully understood from the following detailed description of embodiments thereof, taken together with the drawings, in which:

DETAILED DESCRIPTION OF EMBODIMENTS

Figure 1:
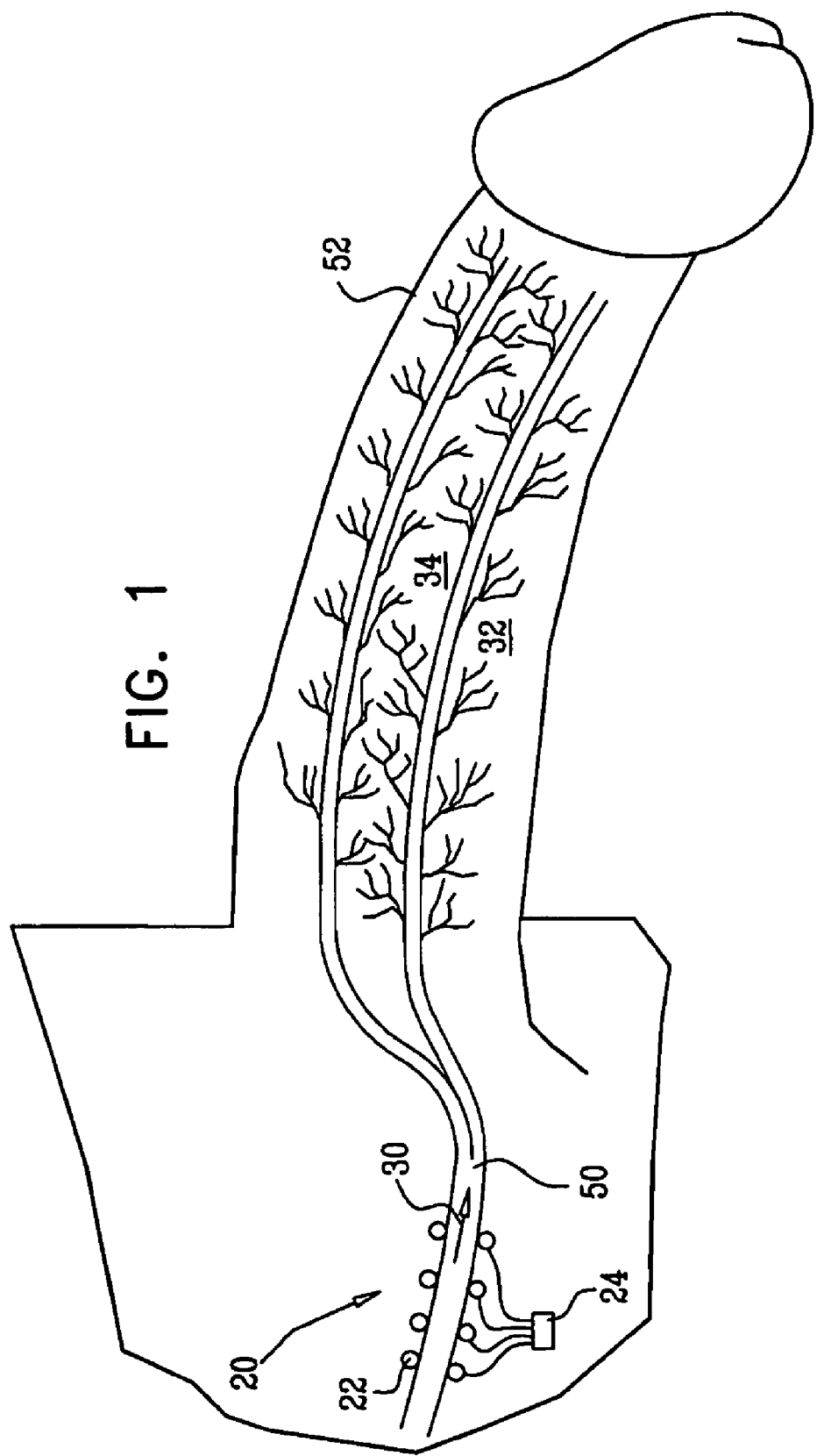
FIG. 1 is a schematic illustration of apparatus for treating erectile dysfunction, in accordance with an embodiment of the present invention.

Reference is now made to FIG. 1, which is a schematic illustration of apparatus 20 for treating erectile dysfunction of a subject, in accordance with an embodiment of the present invention. One or more electrodes 22 are implanted in the vicinity of a blood vessel 50. Typically blood vessel 50 is an artery that supplies the subject's penis 52, for example, the dorsal artery of the penis, the internal iliac artery, or the internal pudendal artery. A control unit 24 is configured to drive the electrodes to drive a current into the vicinity of the blood vessel. The control unit is configured to cause peristaltic pumping of blood toward the penis (i.e., in the direction of arrow 30) by stimulating production of nitric oxide by driving the electrodes to drive the current.

Figure 2A:
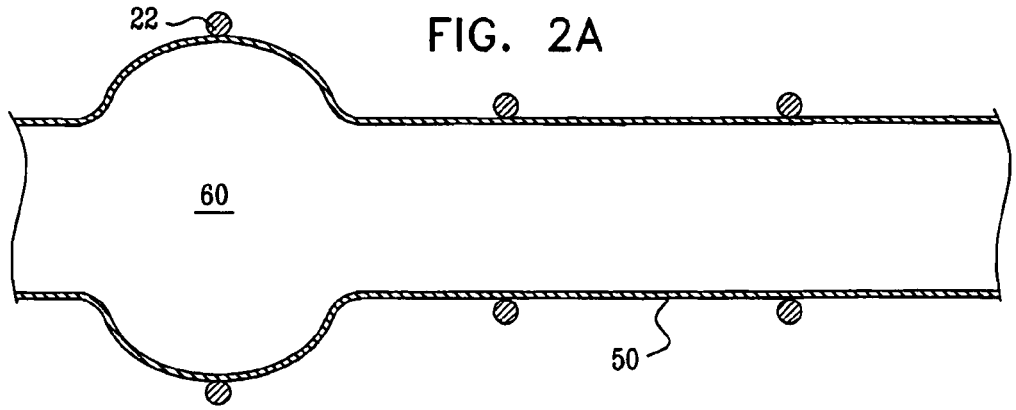
FIGS. 2A-2C are schematic illustrations of a blood vessel that is being dilated peristaltically, in accordance with an embodiment of the present invention.
Figure 2B:
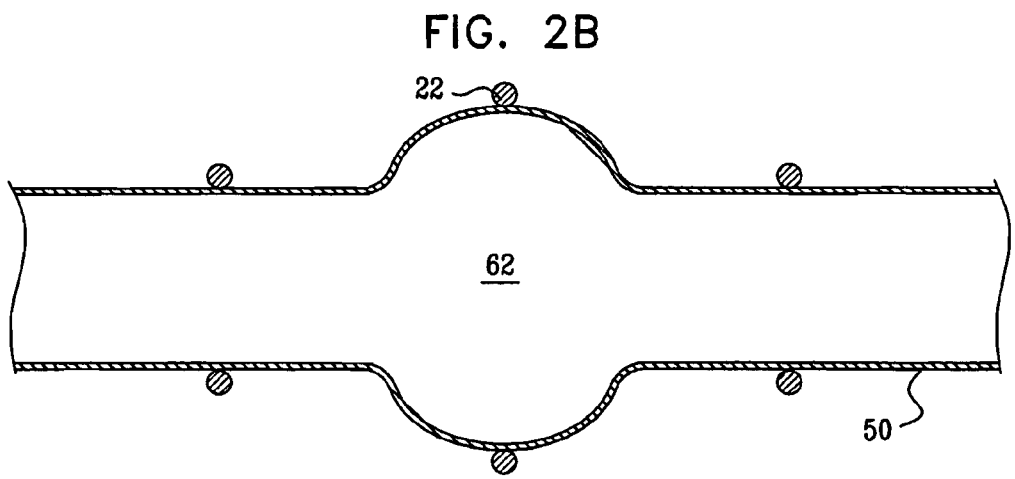
Figure 2C:
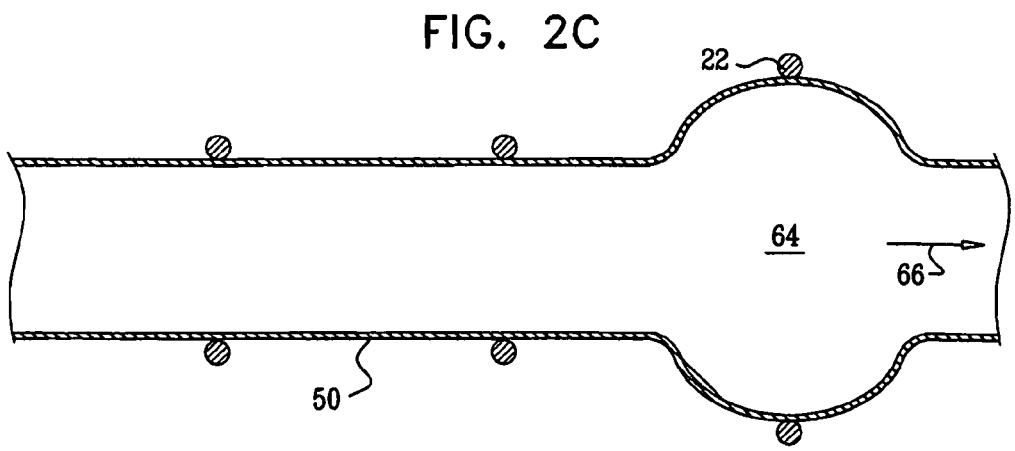

Reference is now made to FIGS. 2A-2C, which show blood vessel 50 being dilated peristaltically, in accordance with an embodiment of the present invention. Typically, upon initiation of pumping, control unit 24 (FIG. 1) causes a region 60 of blood vessel 50 to dilate by driving a current through the proximal-most electrodes of electrodes 22 (as shown in FIG. 2A). The current is sequentially driven through the remaining electrodes, causing regions 62 and 64 to dilate (as shown in FIGS. 2B and 2C respectively), and causing blood to flow in the direction of arrow 66, toward the penis.

In an embodiment (not shown), while region 62 is being dilated, region 60 (which had been dilated) is actively contracted, by applying thereto a contraction-inducing current, e.g., having a frequency of between 40 Hz and 70 Hz. For some applications, the contraction-inducing current has an amplitude of between 5 mA and 20 mA, e.g., between 8 mA and 15 mA. The contraction-inducing current applied to region 60 thus helps to push blood distally that is in dilated region 62. Subsequently, the contraction-inducing current is applied to region 62 while region 64 is being dilated.

In some embodiments, control unit 24 is configured to operate in coordination with a cardiac cycle of the subject, e.g., to peristaltically pump by inducing dilation during systole, and to apply a contraction-inducing current during diastole (analogous to loading a pump during systole, and releasing the stored liquid during diastole). Alternatively, the control unit is configured to operate independently of the cardiac cycle of the subject.

For some applications, control unit 24 is configured to receive an input from the subject and initiate the pumping of blood toward the penis in response to receiving the input. In some embodiments, the control unit comprises a sensor. The control unit is configured to receive an input from the sensor and to initiate the pumping of blood toward the penis in response to receiving the input from the sensor.

Typically, the sensor is configured to detect signals which indicate the desire of the patient to undergo a penile erection. For example, the sensor may comprise a blood flow detector which is configured to respond to an increase of blood flow to the penis. For some applications, the blood flow detector is coupled to another detector which detects the rate of blood flow elsewhere in the body. The control unit processes the information from the two sensors, to determine if the increased blood flow to the penis indicates a desire of the patient to undergo a penile erection. Alternatively or additionally, the sensor comprises a chemical sensor which detects the presence of hormones or other molecules in the patient's body, which are indicative of a desire of the patient to undergo a penile erection. Further alternatively or additionally, the sensor comprises one or more electrodes which detect electrical activity of a nerve that innervates vasculature of the penis. The control unit receives data from the electrodes, and determines when signals are being sent to penile arterial vasculature to dilate the arterial vasculature, and/or when signals are being sent to penile venous vasculature to constrict the venous vasculature.

In some embodiments, blood vessel 50 is a vein that is supplied by blood from the penis of the subject, and electrodes 22 are implanted in the vicinity of the vein. Control unit 24 is configured to reduce outflow of blood from the penis by peristaltically pumping the vein as described hereinabove with respect to peristaltic pumping of arteries. The control unit is configured to peristaltically pump the vein in the opposite direction to the flow of blood out of the penis, and thus to oppose the outflow of blood from the penis. In all other aspects, apparatus 20 is the same as described for when blood vessel 50 is an artery. In some embodiments, electrodes 22 are implanted in a vicinity of one or more arteries that supply the penis, as well as one or more veins that are supplied by blood from the penis. The control unit is configured to treat erectile dysfunction of the subject by (a) increasing the flow of blood into the penis by peristaltically pumping the arteries, and (b) reducing the outflow of blood from the penis by peristaltically pumping the veins. In an embodiment one or both of the arterial or venous peristaltic pumping modes is carried out by causing contraction of the corresponding blood vessels, rather than NO-mediated dilation.

In some embodiments, electrodes 22 are configured to be implanted inside blood vessel 50. Alternatively or additionally, the electrodes are configured to be implanted outside of the blood vessel 50 (as shown in FIGS. 1 and 2A-C). For example, the electrodes may be implanted in the subject's corpus spongiosum 32, or corpus cavernosum 34.

For some applications, electrodes 22 are disposed longitudinally along blood vessel 50 with a longitudinal spacing therebetween of 150%-250% of the local diameter of the blood vessel and/or of 0.5-4 cm, e.g., 2.0-2.5 cm. The spacing may be maintained, for example, by a housing to which the electrodes are coupled (e.g., a flexible stent, or the body of a skin patch) or by sutures or adhesives which couple the electrodes to the blood vessel. As appropriate for the level of peristaltic flow desired, the time for a given peristaltic cycle, i.e., for a peristaltic wave to be generated and to travel along all of the electrodes, typically ranges from about 0.25 second to about 2 seconds.

In some embodiments, electrodes 22 are configured to be placed on skin of the subject, for example, around the outside of the subject's penis 52.

Figure 3:
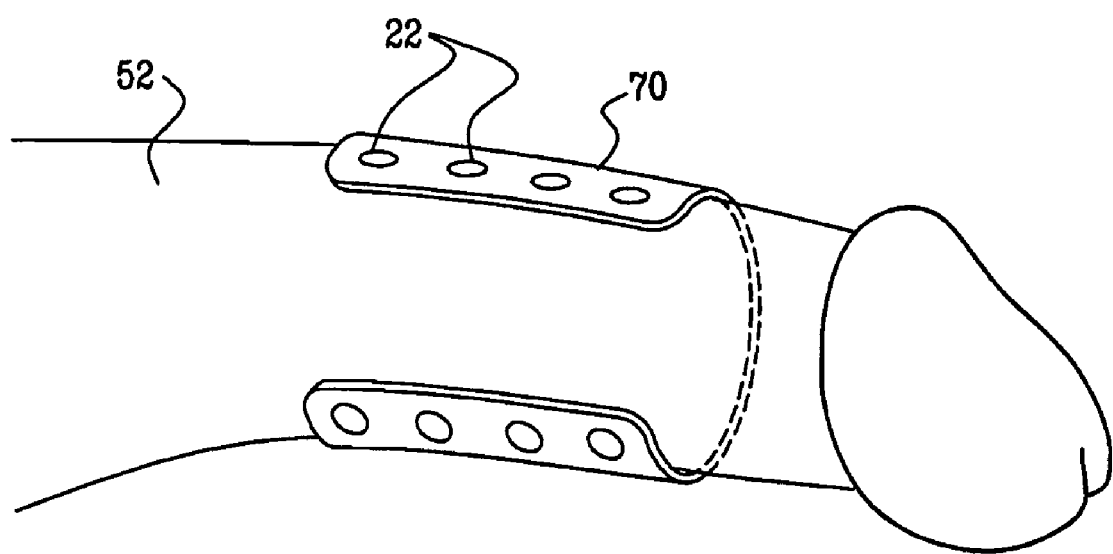
FIG. 3 is a schematic illustration of electrodes disposed on a patch that is wrapped around a penis, in accordance with an embodiment of the present invention.

Reference is now made to FIG. 3, which is a schematic illustration of electrodes 22 disposed on a patch 70, in accordance with an embodiment of the present invention. For some applications, the electrodes are coupled to the subject's skin by placing the patch on the skin. FIG. 3 shows electrodes disposed on a patch that is placed around the outside of the subject's penis 52.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating erectile dysfunction of a subject, comprising:
    a plurality of electrodes configured to be coupled to a vicinity of a blood vessel that carries blood into or out of a penis of the subject; and
    a control unit configured to facilitate erection of the penis by peristaltically pumping blood in the blood vessel by stimulating nitric oxide (NO) production in the vicinity, by driving the electrodes to sequentially drive a current into the vicinity.

2. The apparatus according to claim 1, wherein the blood vessel includes a vein, and wherein the control unit is configured to facilitate the erection by inhibiting blood from leaving the penis by peristaltically pumping the blood.

3. The apparatus according to claim 1, wherein the blood vessel includes an artery, and wherein the control unit is configured to facilitate the erection by peristaltically pumping the blood distally in the artery.

4. The apparatus according to claim 3, wherein the control unit is additionally configured to apply a contraction-inducing current at a site proximal to a site in which the control unit is stimulating nitric oxide production.

5. The apparatus according to claim 3,
further comprising a plurality of venous electrodes configured to be coupled to a vicinity of a vein that is supplied by blood from the penis of the subject,
wherein the control unit is configured to reduce outflow of blood from the penis by peristaltically pumping the vein by stimulating nitric oxide (NO) production in the vicinity of the vein, by sequentially driving the venous electrodes to drive a current into the vicinity of the vein.

6. The apparatus according to claim 3, wherein the control unit is configured to operate independently of a cardiac cycle of the subject.

7. The apparatus according to claim 3, wherein the control unit is configured to drive the electrodes to drive a current having a frequency of 5-15 Hz into the vicinity.

8. The apparatus according to claim 3, wherein the control unit is configured to drive the electrodes to drive a current having an amplitude of 1-5 mA into the vicinity.

9. The apparatus according to claim 3, wherein the plurality of electrodes comprise at least three electrodes, configured to be coupled to respective longitudinal positions along the artery such that a spacing between one of the three electrodes and another one of the three electrodes is between 1 cm and 4 cm.

10. The apparatus according to claim 3, wherein the plurality of electrodes comprise at least three electrodes, and wherein the apparatus further comprises a housing to which the at least three electrodes are coupled, which is configured to maintain a longitudinal distance between one of the three electrodes and another one of the three electrodes that is between 1 cm and 4 cm.

11. The apparatus according to claim 3, wherein the control unit is configured to set a duration of one cycle of peristaltic pumping to be between 0.25 second and 2 seconds.

12. The apparatus according to claim 3, wherein the control unit is configured to operate in coordination with a cardiac cycle of the subject.

13. The apparatus according to claim 12, wherein the control unit is configured to peristaltically pump the blood by stimulating the nitric oxide production during systole, and to apply a contraction-inducing current into the vicinity during diastole.

14. The apparatus according to claim 3, wherein the plurality of electrodes are configured to be placed on skin of the subject and to drive the current through the skin.

15. A method for treating erectile dysfunction of a subject, comprising:
coupling a plurality of electrodes to a vicinity of a blood vessel that carries blood into or out of a penis of the subject; and
facilitating erection of the penis by peristaltically pumping blood in the blood vessel by stimulating nitric oxide (NO) production in the vicinity by driving the electrodes to sequentially drive a current into the vicinity.

16. The method according to claim 15, wherein the blood vessel includes a vein, and wherein peristaltically pumping the blood comprises reducing outflow of blood from the penis by peristaltically pumping the blood.

17. The method according to claim 15, wherein the blood vessel includes an artery, and wherein facilitating the erection comprises peristaltically pumping blood in the artery by stimulating the nitric oxide production.

18. The method according to claim 17, further comprising applying a contraction-inducing current at a site proximal to a site of the stimulating of the nitric oxide production.

19. The method according to claim 17, wherein coupling the plurality of electrodes comprises coupling at least three electrodes to the artery, at respective longitudinal positions along the artery, such that a spacing between one of the three electrodes and another one of the three electrodes is between 1 cm and 4 cm.

20. The method according to claim 17, wherein driving the electrodes comprises setting a duration of one cycle of peristaltic pumping to be between 0.25 second and 2 seconds.

* * * * *